United States Patent [19]

Worthington et al.

[11] 4,269,845

[45] * May 26, 1981

[54] TRIAZOLE AND IMIDAZOLE COMPOUNDS AND THEIR USE AS FUNGICIDES AND PLANT GROWTH REGULATING AGENTS

[75] Inventors: Paul A. Worthington; Margaret C. Shephard, both of Maidenhead, England

[73] Assignee: Imperial Chemical Industries Limited, London, England

[*] Notice: The portion of the term of this patent subsequent to Dec. 19, 1995, has been disclaimed.

[21] Appl. No.: 901,125

[22] Filed: Jan. 20, 1978

[30] Foreign Application Priority Data

Jan. 20, 1977 [GB] United Kingdom ................. 2304/77
Oct. 26, 1977 [GB] United Kingdom ............... 44540/77

[51] Int. Cl.$^3$ ..................... A01N 43/50; A01N 43/64; C07D 233/60; C07D 249/08
[52] U.S. Cl. ........................ 424/269; 71/67; 71/76; 71/92; 424/245; 424/273 R; 548/101; 548/262; 548/336; 548/341
[58] Field of Search ....................... 548/101, 262, 341; 424/245, 269, 273 R

[56] References Cited

U.S. PATENT DOCUMENTS

| 3,843,667 | 10/1974 | Cupery | 548/101 |
| 4,130,409 | 12/1978 | Shephard et al. | 548/262 |

FOREIGN PATENT DOCUMENTS

| 2431407 | 8/1973 | Fed. Rep. of Germany | 424/269 |
| 2734426 | 2/1978 | Fed. Rep. of Germany | 424/269 |
| 2802496 | 7/1978 | Fed. Rep. of Germany | 424/269 |
| 2303475 | 8/1976 | France | 548/262 |
| 2323689 | 8/1977 | France | 548/262 |
| 7507629 | 6/1975 | Netherlands | 548/262 |
| 7609439 | 6/1977 | Netherlands | 548/262 |
| 7613372 | 7/1977 | Netherlands | 548/262 |
| 7613784 | 8/1977 | Netherlands | 548/262 |

*Primary Examiner*—Alton D. Rollins
*Attorney, Agent, or Firm*—Cushman, Darby & Cushman

[57] ABSTRACT

This invention relates to heterocyclic compounds which are 1,2,4-triazole and imidazole compounds, to a process for preparing them, to compositions comprising them, to a method of combating fungal diseases in plants using them and to a method of regulating the growth of plants using them.

12 Claims, No Drawings

TRIAZOLE AND IMIDAZOLE COMPOUNDS AND THEIR USE AS FUNGICIDES AND PLANT GROWTH REGULATING AGENTS

The invention provides a compound of general formula (I):

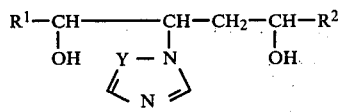

wherein each of $R^1$ and $R^2$, which may be the same or different, is alkyl, haloalkyl or optionally substituted aryl (e.g. phenyl), and Y is =N— or =CH—; or an ester, an ether, an acid addition salt or a metal complex thereof.

The compounds of the invention contain chiral centres. The compounds are generally obtained in the form of racemic mixtures. However these of other mixtures can be separated into the individual isomers by methods known in the art e.g. chromatography.

The alkyl groups, which can be straight or branched chain, preferably have 1 to 6 carbon atoms; examples are methyl, ethyl, propyl (n- or i-propyl) and butyl (n-, i- or t-butyl).

The aryl group suitably contains 6 to 12 carbon atoms. The aryl (e.g. phenyl) group can be substituted with halogen, $C_{1-4}$ alkyl [e.g. methyl, ethyl, propyl (n- or i-propyl) and butyl (n-, i- or t-butyl)], halo-($C_{1-4}$ alkyl), phenyl, halophenyl (e.g. chlorophenyl), cycloalkyl, nitro, cyano, $C_{1-6}$ alkoxy (e.g. methoxy or ethoxy), ($C_{1-4}$ alkylene)dioxy (e.g. methylenedioxy), ($C_{1-4}$ alkoxy) ($C_{1-4}$ alkyl) [e.g. 2-methoxy- or ethoxy-ethyl], mercapto, ($C_{1-4}$ alkyl) thio [e.g. methyl- or ethyl-thio], ($C_{1-4}$ alkyl) sulphonyl [e.g. methyl- or ethyl-sulphonyl], ($C_{1-4}$ halo-alkyl) sulphonyl [e.g. trifluoromethylsulphonyl], phenyl-sulphonyl, unsubstituted or mono- or di-($C_{1-4}$ alkyl) substituted sulphamoyl or carbamoyl, carboxy, ($C_{1-4}$ alkoxy)-carbonyl [e.g. methoxy- or ethoxy-carbonyl], unsubstituted or mono- or di- ($C_{1-4}$ alkyl) substituted amino, ($C_{1-6}$ alkanoyl)amino, N-($C_{1-4}$ alkyl)-substituted ($C_{1-6}$ alkanoyl)-amino, formylamino, N-($C_{1-4}$ alkyl)-substituted formylamino, phenylethyl, phenoxy or benzyloxy. A suitable alkanoyl is acetyl or propionyl. The aryl group can have more than one ring substituent; examples of polysubstituted groups are those substituted with up to the maximum possible number (especially 1, 2 or 3) of for example halogen (particularly chlorine) atoms and/or nitro, methyl or methoxy groups.

Examples of suitable aryl groups are phenyl itself, chlorophenyl (e.g. o-, m- or p-chlorophenyl), dichlorophenyl (e.g. 2,4- or 2,6-dichlorophenyl), fluorophenyl (e.g. o-, m- or p-fluorophenyl), nitrophenyl (e.g. p-nitrophenyl), methoxyphenyl (e.g. o-methoxyphenyl) and tolyl (e.g. p-tolyl).

Preferably the haloalkyl group contains 1 to 3 halogen atoms; examples are 2-chloroethyl, trifluoromethyl or trichloromethyl.

The halogen can be fluorine, chlorine, bromine or iodine.

Suitable salts are salts with inorganic or organic acids, e.g. hydrochloric, nitric, sulphuric, toluenesulphonic, acetic or oxalic acid. The esters and ethers can be mono- or di- esters and ethers; alternatively, the compound can be one wherein one hydroxy group is in ether form and the other is in ester form. The esters are suitably alkanoates (e.g. acetates) and the ethers are suitably alkyl (e.g. methyl or ethyl), aryl (e.g. phenyl) or aralkyl (e.g. benzyl) ethers. The metal complex is suitably one including copper, zinc, manganese or iron.

Specific examples of the compounds are given in Table 1.

TABLE I

| COMPOUND NO | $R^1$ | $R^2$ | Y | MELTING POINT (°C.) |
|---|---|---|---|---|
| 1 | t-Bu | p-Cl—$C_6H_4$— | =N— | 160°–163° |
| 2 | $C_6H_5$— | $C_6H_5$— | =N— | 60° |
| 3* | i-Pr | p-Cl—$C_6H_4$— | =N— | gum |
| 4* | i-Pr | p-Cl—$C_6H_4$— | =N— | gum |
| 5* | i-Pr | p-Cl—$C_6H_5$ | =N— | gum |
| 6 | t-Bu | t-Bu | =N— | 153°–154° |
| 7 | n-Pr | p-Cl—$C_6H_4$ | =N— | oil |
| 8 | Et | p-Cl—$C_6H_4$ | =N— | oil |
| 9$^x$ | i-Pr | p-F—$C_6H_4$ | =N— | gum |
| 10$^x$ | i-Pr | p-F—$C_6H_4$ | =N— | gum |
| 11$^x$ | i-Pr | p-F—$C_6H_4$ | =N— | gum |
| 12$^o$ | i-Pr | o-MeO—$C_6H_4$ | =N— | gum |
| 13$^o$ | i-Pr | o-MeO—$C_6H_4$ | =N— | gum |
| 14$^o$ | i-Pr | o-MeO—$C_6H_4$ | =N— | gum |

*Compounds 3 and 4 are diastereoisomers of each other; Compound 5 is a mixture of these diastereoisomers.
$^x$Compounds 9, 10 and 11 are diastereoisomers of each other.
$^o$Compounds 12, 13 and 14 are diastereoisomers of each other.

The compounds (and the salts and complexes) of the invention may be made by reducing (preferably at 0° to 100° C. and for 1 to 12 hours) a diketone or ketoalcohol of general formula (II):

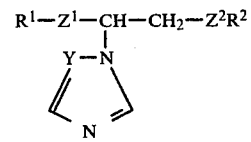

wherein Y, $R^1$ and $R^2$ are as defined above, and either both the groups $Z^1$ and $Z^2$ are C=O or one is C=O and the other is CHOH, or a salt or metal complex thereof, with for example a metal hydride reducing agent (e.g. lithium aluminium hydride, sodium borohydride or aluminium isopropoxide) in an inert polar solvent (e.g. water or ethanol).

The starting materials for the process may be made by reacting imidazole or 1,2,4-triazole or a salt thereof with the appropriate γ-diketone or ketoalcohol in a high boiling hydrocarbon solvent (e.g. toluene or xylene) at refluxing temperatures. Thus for example 1,2,4-triazole may be reacted with a compound of general formula (III):

$$R^1—Z^1—CH=CH—Z^2—R^2$$

where $R^1$, $R^2$, $Z^1$ and $Z^2$ are as defined hereinabove.

The reduction generally involves dissolving the reactants in a solvent such as diethyl ether or tetrahydrofuran (for lithium aluminium hydride reduction) or a hydroxylic solvent (for sodium borohydride reduction). The temperature at which the reaction may be carried out will depend on the reactants and solvent but generally the reaction mixture is heated under reflux. The reaction product is then isolated by extraction into a convenient solvent after acidification with dilute mineral acid. After removal of the solvent in vacuo, the product may be crystallised from a convenient solvent.

The compounds of general formua (III) may be made by any of the methods set out in literature.

The salts, metal complexes, ethers and esters of the compounds of general formula (I) can be prepared from the latter in known manner. For example, the complexes can be made by reacting the uncomplexed compound with a metal salt in a suitable solvent.

The compounds are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

Erysiphe graminis (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Cercospora arachidicola* on peanuts and other Cercospora species on for example sugar beet, bananas and soya beans *Botrytis cinerea* (grey mould) on tomatoes, strawberries, vines and other hosts

*Phytophthora infestans* (blight) on tomatoes

*Venturia inaequalis* (scab) on apples

Some of the compounds are active as seed dressings against: Fusarium spp., Septoria spp., Tilletia spp. (i.e. bunt, a seed borne disease of wheat), Ustilago spp., and Helminthosporium spp (e.g. *Helminthosporium gramineum* and *H. sativum*) on cereals.

The compounds also have herbicidal, algicidal, antibacterial and antiviral activities as well as plant growth regulating activities.

The plant growth regulating effects of the compounds, salts, complexes, ethers and esters are manifested as for example a stunting or dwarfing effect on the vegetative growth of woody and herbaceous mono- and di-cotyledonous plants. Such stunting or dwarfing may be useful, for example, in cereals and soya bean where reduction in stem growth may reduce the risk of lodging. Compounds which induce stunting or dwarfing may also be useful in modifying the growth of sugar cane thereby increasing the concentration of sugar in the cane at harvest. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum,* and perenne, *Agrostis tenuis, Cynodon dactylon* (Bermuda grass), *Dactylis glomerata,* Festuca spp. (e.g. *Festuca rubra*) and Poa spp. (e.g. *Poa pratense*). At least some of the compounds will stunt grasses without significant phytotoxic effects and without deleteriously affecting the appearance (particularly the colour) of the grass; this makes such compounds attractive for use on ornamental lawns and on grass verges. They may also have an affect on flower head emergence in for example grasses. The compounds can also stunt weed species present in the grasses; examples of such weed species are sedges (e.g. Cyperus spp.) and dicotyledonous weeds. The growth of non-crop vegetation (e.g. weeds or cover vegetation) can be retarded thus assisting in the maintenance of plantation and field crops. In orchards, particularly orchards subject to soil erosion, the presence of grass cover is important. However excessive grass growth requires substantial maintenance. The compounds of the invention could be useful in this situation as they could restrict growth without killing the plants (the death of the plants could lead to soil erosion).

The plant growth regulating effect may manifest itself in an increase in crop yield.

Other plant growth regulating effects caused by the compounds include alteration of leaf angle and promotion of tillering in plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. The treatment of plants with the compounds of the invention can lead to the leaves developing a darker green colour.

Further the compounds may inhibit the flowering of sugar beet and thereby may increase sugar yield. They may also reduce the size of sugar beet without reducing significantly the sugar yield thereby enabling an increase in planting density to be made.

The compounds could also be used to restrict the vegetative growth of cotton thereby leading to an increase in cotton yield.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds may be used as such for fungicidal and plant growth regulating purposes but are more conveniently formulated into compositions for such usage. The invention thus provides also a fungicidal or plant growth regulating composition comprising a compound of general formula (I) or a salt, complex, ether or ester thereof as hereinbefore defined, and a carrier or diluent.

The invention also provides a method of combating fungal diseases in a plant, which method comprises applying to the plant, to seed of the plant or to the locus of the plant or seed a compound or salt, complex, ether or ester thereof as hereinbefore defined.

It also provides a method of regulating the growth of a plant, which method comprises applying to the plant, to seed of the plant or to the locus of the plant or seed a compound or salt, complex, ether or ester thereof as hereinbefore defined.

The compounds, salts, complexes, ethers and esters can be applied in a number of ways, for example they can be formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt, metal complex, ether or ester thereof.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or nonionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity [e.g. other growth stimulating substances such as the gibberellins (e.g. $GA_3$, $GA_4$ or $GA_7$), the auxins (e.g. indoleacetic or indolebutyric acid) and the cytokinins (e.g. kinetin, diphenylurea, benzimidazole and benzyladenine) and other compounds having complementary fungicidal or insecticidal activity], as well as stabilising agent(s), for example epoxides (e.g. epichlorhydrin). The other fungicidal compound can be one which is capable of combating ear diseases of cereals (e.g. wheat) such as Septoria, Gibberella, Helminthosporium and the sooty mould complex; examples of such compounds are benomyl, carbendazole (BCM) and captafol. Alternatively, it can be one which is capable of combating seed- and soil-borne diseases; examples of such compounds are Maneb and Captan.

The following Examples illustrate the invention; the temperatures are given in degrees Centigrade (°).

EXAMPLE 1

4-(1,2,4-Triazol-1-yl)-2,2-dimethyl-6-p-chlorophenyl-3,6-diol. (Compound 1)

Stage 1. 2,2-Dimethyl-6-p-chlorophenyl-hex-4-en-3,6-dione (0.05 mol) and 1,2,4-triazole (0.05 mol) were suspended in toluene (200 ml) and refluxed for 24 hours. After cooling to room temperature, the excess triazole was filtered off and the organic layer washed with water (2×150 ml) and dried over anhydrous sodium sulphate. Removal of the solvent gave a brown solid which on recrystallisation from petrol/chloroform gave 4-(1,2,4-triazol-1-yl)-2,2-dimethyl-6-p-chlorophenyl-hexan-3,6-dione (75% yield) as colourless needles m.p. 116°–119°.

Stage 2. 4-(1,2,4-Triazol-1-yl)-2,2-dimethyl-6-p-chlorophenyl-hexan-3,6-dione (0.0063 mol) was dissolved in methanol (100 ml) and sodium borohydride (0.013 mol) was added portionwise. The solution was then refluxed for 1 hour, cooled to room temperature and the solvent removed in vacuo. Acidification with 2NHCl (50 ml) gave a white solid which on recrystallisation from petroleum ether/chloroform gave the title compound (80% yield) as colourless crystals, m.p. 160°–163°.

appropriate environment to allow infection to take place and then incubated until the disease was ready for assessment. The period between inoculation and assessment varied from 4 to 14 days according to the disease and evironment.

The disease control was recorded by the following grading:
4 = No disease
3 = 0–5%
2 = 6–25%
1 = 26–60%
0 = <60%

The results are shown in Table II.

TABLE II

| COMPOUND NUMBER | PUCCINIA RECONDITA (WHEAT) | PHYTOPHTHORA INFESTANS (TOMATO) | PLASMOPARA VITICOLA (VINE) | PIRICULARIA ORYZAE (RICE) | BOTRYTIS CINEREA (TOMATO) | ERYSIPHE GRAMINIS (BARLEY) | CERCOSPORA ARACHIDICOLA (PEANUT) |
|---|---|---|---|---|---|---|---|
| 1 | 3 | 4 | 0 |   | 4 | 2 |   |
| 2 | 2 | 1 | 0 | 2 | 0 | 4 |   |
| 3 | 2 | 0 | 3 |   | 0 | 4 |   |
| 4 | 3 | 0 | 0 | 0 | 0 | 3 | 0 |
| 5 | 3 | 0 | 3 |   | 0 | 3 |   |
| 6 | 4 | 0 | 2 | 2 | 1 | 4 |   |
| 7 | 2 | 0 | 0 | 2 | 0 | 4 |   |
| 8 | 0 | 3 | 0 | 1 | 1 | 3 |   |
| 10 | 3 | 0 | 0 | 0 | 1 | 4 | 3 |

EXAMPLE 2

The compounds were tested against a variety of foliar fungal diseases of plants. The technique employed was as follows:

The plants were grown in John Innes Potting Compost (No. 1, or Seed, as appropriate) in 4 cm diameter mini-pots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the foliage diseases, 100 p.p.m. a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and to the foliage (by spraying) one or two days before the plant was inoculated with the diseases. An exception was the test on *Erysiphe graminis*, in which the plants were inoculated 24 hours before treatment. After inoculation, the plants were put into an

EXAMPLE 3

This Example illustrates the plant growth regulating properties of the compounds. The compounds were applied in the form of a 4000 p.p.m. solution in distilled water and the solution was then applied to the foliage of young seedlings of wheat, barley, maize, rice, Lolium rye grass, soya, cotton, groundnut, lettuce, tomato, Mung bean and French bean. The experiments were replicated twice. After 21 days from treatment, the plants were assessed for plant growth regulating effects and phytotoxic symptoms.

Table III shows the stunting effect of the compounds on the vegetative growth using the following grading:
0 = ≦20% retardation
1 = 21–40% retardation
2 = 41–60% retardation
3 = 61–80% retardation If no figure is given, the compound was substantially inactive as a stunting agent.

Additional plant growth regulating properties are indicated as follows:
G = darker green leaf colour
A = apical effect
T = tillering effect The symbol "-" is used to indicate that the compound has not been tested on that particular crop.

TABLE III

| COMPOUND NO | WHEAT | BARLEY | MAIZE | RICE | LOLIUM RYE GRASS | SOYA | COTTON | GROUND NUT | LETTUCE | TOMATO | MUNG BEAN | FRENCH BEAN |
|---|---|---|---|---|---|---|---|---|---|---|---|---|
| 1 | 1G | 1G |   |   | 1G | 0GA | 1GA |   | GA | A | A | 1A |
| 2 |   |   |   |   | — | 3 | — |   |   | 1 | — | A |
| 3 | — | — | — | — | — | — | — | — | — | — | — | — |
| 4 | 1 | 1 |   |   |   | 1GA | A | — | 1A | 1 | — | 1GA |
| 5 | G | G | 2 |   |   | 2A | 3GA | — | 1A | 1GA | — | 3GA |
| 6 |   | 1 |   | 1 | — | 1GA | 3A | — | 1 | 3GA | — | 3A |
| 7 |   |   |   |   | — |   |   | — | 2A | 2A | — | 1A |
| 8 |   |   |   |   | — |   | 2 | — |   |   | — | 2 |
| 9 |   |   |   |   |   |   |   |   |   |   |   | 1GA |
| 10 |   |   |   |   |   | 1GA | 1A |   | 2A |   |   | 1GA |

TABLE III-continued

| COMPOUND NO | WHEAT | BARLEY | MAIZE | RICE | LOLIUM RYE GRASS | SOYA | COTTON | GROUND NUT | LETTUCE | TOMATO | MUNG BEAN | FRENCH BEAN |
|---|---|---|---|---|---|---|---|---|---|---|---|---|
| 11 | | | | | | A | 1 | | 2A | 1 | | A |

We claim:

1. A compound of general formula (I):

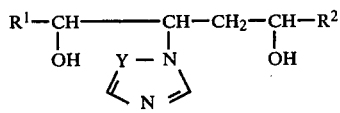

wherein each of $R^1$ and $R^2$, which may be the same or different is $C_{1-6}$ alkyl, halo ($C_{1-6}$ alkyl) or phenyl optionally substituted with up to three substituents selected from the class consisting of halogen, nitro, $C_{1-4}$ alkyl, and $C_{1-4}$ alkoxy, and Y is =N— or =CH—; or an alkanoate ester, an alkyl, phenyl or benzyl ether, an acid addition salt or a copper, zinc, manganese or iron complex thereof.

2. A compound as claimed in claim 1 wherein each of $R^1$ and $R^2$, which may be the same or different is $C_{1-6}$ alkyl, fluoro- or chloro-($C_{1-6}$ alkyl), or phenyl optionally substituted with one halogen, nitro, $C_{1-6}$ alkyl or $C_{1-6}$ alkoxy.

3. A compound as claimed in claim 2 wherein each of $R^1$ and $R^2$, which may be the same or different, is ethyl, propyl, butyl, phenyl, monochlorophenyl, monofluorophenyl, or monomethoxyphenyl.

4. A compound as claimed in claim 3 wherein $R^1$ is ethyl, i-propyl, t-butyl or phenyl, $R^2$ is t-butyl, phenyl, p-chlorophenyl, p-fluorophenyl or o-methoxyphenyl, and Y is =N—.

5. A fungicidal composition consisting essentially of, as active ingredients, a fungicidally effective amount of a compound, ester, ether, salt or complex as claimed in claim 1, and a carrier for the active ingredient.

6. A fungicidal composition consisting essentially of, as active ingredients, a fungicidally effective amount of a compound, as claimed in claim 2, and a carrier for the active ingredient.

7. A fungicidal composition consisting essentially of, as active ingredients, a fungicidally effective amount of a compound, as claimed in claim 3, and a carrier for the active ingredient.

8. A fungicidal composition consisting essentially of, as active ingredients, a fungicidally effective amount of a compound, as claimed in claim 4, and a carrier for the active ingredient.

9. A method of combating fungal diseases in a plant, the method consisting essentially of the step of applying to the plant, to seed of the plant or to the locus of the plant or seed, a fungicidally effective amount of a compound, alkanoate ester, alkyl, phenyl or benzyl ether, acid addition salt or copper, zinc, manganese or iron complex as claimed in claim 1.

10. A method of combating fungal diseases in a plant, the method consisting essentially of the step of applying to the plant, to seed of the plant or to the locus of the plant or seed, a fungicidally effective amount of a compound, as claimed in claim 2.

11. A method of combating fungal diseases in a plant, the method consisting essentially of the step of applying to the plant, to seed of the plant or to the locus of the plant or seed, a fungicidally effective amount of a compound, as claimed in claim 3.

12. A method of combating fungal diseases in a plant, the method consisting essentially of the step of applying to the plant, to seed of the plant or to the locus of the plant or seed, a fungicidally effective amount of a compound, as claimed in claim 4.

* * * * *